United States Patent [19]

Hakki et al.

[11] Patent Number: 5,727,558
[45] Date of Patent: Mar. 17, 1998

[54] NONINVASIVE BLOOD PRESSURE MONITOR AND CONTROL DEVICE

[76] Inventors: A-Hamid Hakki; Said I. Hakky, both of 8547 Merrimoor Blvd., E., Largo, Fla. 34647-3145; Perry B. Hudson, 2225 Park St., North, St. Petersburg, Fla. 33710

[21] Appl. No.: 601,259

[22] Filed: Feb. 14, 1996

[51] Int. Cl.$^6$ .................................................. A61B 5/02
[52] U.S. Cl. .............................. 128/672; 607/44; 601/2
[58] Field of Search .................... 128/660.03, 668–673, 128/677, 687, 903; 600/9, 13, 17; 607/1, 2, 3, 44, 60, 97, 115, 154; 601/2

[56] References Cited

U.S. PATENT DOCUMENTS

| | | | |
|---|---|---|---|
| 3,636,941 | 1/1972 | Guevrekian | 128/683 |
| 3,645,267 | 2/1972 | Hagfors | 607/44 |
| 3,650,277 | 3/1972 | Sjostrand et al. | 607/44 |
| 3,735,756 | 5/1973 | Richards et al. | 607/3 |
| 4,425,920 | 1/1984 | Bourland et al. | 128/672 |
| 5,178,152 | 1/1993 | Ozawa | 128/680 |
| 5,433,736 | 7/1995 | Nilsson | 607/60 |

OTHER PUBLICATIONS

Webster's II New Riverside University Dictionary, The Riverside Publishing Co., 1994, p. 232.

Bilgutay et al., "A New Concept in the treatment of Hypertension Utilizing an Implantable Electronic Device," Amer. Soc. Artif. Organs, vol. X, 1964, pp. 387–393.

*Primary Examiner*—Jennifer Bahr
*Assistant Examiner*—Bryan K. Yarnell
*Attorney, Agent, or Firm*—John Lezdey

[57] ABSTRACT

A noninvasive blood pressure monitoring and controlling device is provided which selectively stimulates the human body's own baro-receptors with electromagnetic or ultrasonic wave energies.

9 Claims, 1 Drawing Sheet

NONINVASIVE BLOOD PRESSURE MONITOR AND CONTROL DEVICE

BACKGROUND OF THE INVENTION

1. Field of the Invention

The present invention relates to monitoring and controlling high blood pressure by the stimulation of the human body's own baro-receptors with electromagnetic or ultrasonic wave energies.

2. Description of the Prior Art

Hypertension or abnormally high arterial blood pressure is a serious health hazard. Hypertension is the leading cause of cerebrovascular accidents (stroke) and is a major risk factor for coronary artery disease and myocardial infarction (heart attack) as well as heart failure and renal damage. More than 50 million Americans had hypertension according to estimates in 1983.

The treatment of high blood pressure by the prior art is by medications such as calcium blockers, these agents tend to relax the smooth muscle around the arteries. Other medications are beta-adrenergic blockers, which block the release of certain type of chemicals that produce muscle spasms of the arteries, resulting in high blood pressure. Yet other types called ACE inhibitors exert their blocking effect on hormones secreted by the arteries of the kidney that causes spasms of the smooth muscle surrounding the blood vessels. Diuretics have been used in the treatment of hypertension by enhancing the excretion of sodium by the kidneys and thereby reducing the effective blood volume and blood pressure. Other anti-hypertensive agents act by depleting or inhibiting the effect of neuro-transmitters such as norepinephrine either in the central or peripheral nervous system. All such treatments are expensive and generally have many side effects. In addition medication has to be taken at least once a day and often in combinations for long durations and thus become an expensive proposition.

Blood pressure control is related to the caliber and responsive of the blood vessels. Blood pressure is controlled by the chemo-receptors as described above and baro-receptors. In certain instances, such as, during exercise and in stressful situations the body produces higher blood pressure. Here epinephrine, nor-epinephrine corticosteroid are secreted from the adrenal glands. Other hormones are secreted by other endocrine glands. These hormones exert their influence on the motor end plate of the smooth muscle surrounding the arteries and cause the arteries to contract, thus increasing the blood pressure. The motor end plates contain and release chemical compounds that cause the contraction or relaxation of the smooth muscle surrounding the arteries. These are called chemo-receptors. The body also has a protective mechanism called baro-receptors such as those situated at the bifurcation of each of the two carotid arteries. These baro-receptors are activated by high blood pressure. The high blood pressure will stretch nerve endings at the baro-receptors and send electric impulses to relax the smooth muscles surrounding the blood vessels. There are many baro-receptors scattered throughout the arterial system.

Hardening of the arteries also causes high blood pressure. The hardening is called atherosclerosis. It is postulated that the arteries go into spasm off and on for years, then the arteries lose their elasticity and become hard or rigid, thus causing permanent high blood pressure. These arteries do relax by the effect of medications on the chemo-receptors. These hardened arteries also are relaxed by baro-receptors. In certain cases high doses of drugs are given to relieve the effects of severe hardening of the arteries.

SUMMARY OF THE INVENTION

Broadly, the present invention is directed to a portable apparatus to be worn by a patient and methods which employ a baro-receptor stimulator device for therapy or treatment of hypertension or high blood pressure or episodes of the disease through baro-receptor stimulation. The modulating signals applied to the baro-receptors located at the upper part of each side of the neck to stimulate the release of baro-receptors and to inhibit the build-up of blood pressure. It should be emphasized that although the preferred baro-receptor site is the neck for application of the modulating signals, effective treatment may be achieved through application of the stimulus to one or more other baro-receptor sites located throughout the arterial system and such treatment is deemed to be within the scope of the present invention.

In accordance with this invention, the therapy is delivered in a manner to monitor the patient's baro-receptors, particularly those located at each side of the upper part of the neck in a predetermined manner to treat and relieve the effects of high blood pressure, and the baro-receptor stimulator device is programmed by the attending physician to provide the desired therapeutic modality for that purpose.

More particularly the invention is defined by the following: noninvasive blood pressure monitor and control apparatus comprising a programmable baro-receptor stimulator device adapted to receive input monitoring signals and to generate a programmed output signal upon activation of said device and a noninvasive conductive lead assembly connectable at its proximal end to a device to receive the programmed output signal thereof and having a sensor at its distal end noninvasively attached to the skin surface on each side of the neck of the patient for stimulation of the baro-receptor to modulate the blood pressure, characterized in that the apparatus further includes:

an electrical power source, sensor means coupled to the baro-stimulator device for detecting blood pressure, activator means responsive to detection of blood pressure parameters for activating the baro-receptor stimulator device to apply its programmed output signal to said sensor means, said baro-receptor stimulator device including means rendering the output signal parameter thereof programmable only within respective ranges preselected for controlling the blood pressure according to the specific parameters programmed.

The output signals to stimulate the baro-receptors may be electromagnetic waves or ultrasonic waves.

It is therefore a principal object of the present invention to provide a noninvasive device for monitoring and controlling blood pressure by applying electromagnetic or ultrasonic wave energies to activate the baro-receptor inherent in the arterial system.

Another object of this invention is to provide methods and apparatus for treating and controlling high blood pressure by sensing a predetermined detectable event and thereafter automatically or manually effecting modulation of the baro-receptors through the application of a preselected stimulus to the patient's baro-receptor reservoirs.

Yet another object is to provide a high blood pressure apparatus that is of small size and portable.

A further object is to provide a method for controlling blood pressure without the use of drugs.

A still further object is to provide an apparatus for monitoring and controlling blood pressure by automatic or manual activation to modulate the baro-receptor activity through the application of preselected stimuli to the patient's baro-receptor reservoirs, the apparatus being automatically powered down after successful treatment or control of a raised blood pressure episode so as to conserve battery power.

Other and further objects of this invention will be apparent from the drawings and the following detailed description thereof which is set forth for the purpose of explaining the invention and is not regarded as necessarily limiting the scope of the invention which is defined in the appended claims.

BRIEF DESCRIPTION OF THE DRAWINGS

Specific implementation for the invention will be described by way of example, with reference to the accompanying drawings, in which.

DESCRIPTION OF THE PREFERRED EMBODIMENTS

The noninvasive blood pressure monitor and control apparatus according to this invention (FIGS. 1 and 2) utilizes a conventional microprocessor and other standard electrical and electronic components and many communicate with a programmer and/or monitor located externally and remotely from the patient's body for controlling or indicating the various states of the device. The apparatus of this invention also includes means for conserving energy which is important for any battery operated device and further includes means for providing various safety functions such as preventing accidental reset of the device. Still further the apparatus includes a lead assembly 27 comprising a lead system 23 and 26 for monitoring and for applying the output signal of the baro-receptor stimulator device 10 and particularly to the baro-receptors situated at the upper part of each side of the patient's neck to control high blood pressure.

In conjunction with its microprocessor-based logic and control circuitry, the baro-stimulator device 10 along with other external circuitry includes detection circuitry for sensing an event indicative of the onset of change in the blood pressure of the patient to trigger automatic delivery of the stimulated signal. For example, the surface electrodes 12 sense specific characteristics of the patient's blood pressure for triggering the therapy. The baro-receptor stimulator device 10 is designed, implemented, and programmed to deliver a selectively patterned stimulating signal to modulate the electrical activity of the baro-receptor to treat and control the blood pressure.

Figure 1:
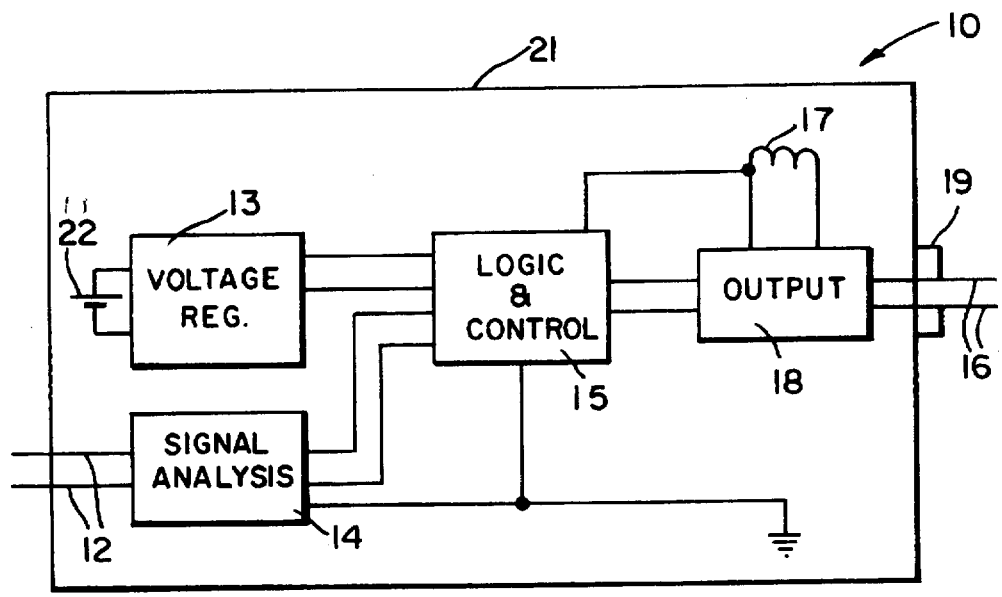
FIG. 1 is a block-circuit diagram of the baro-receptor stimulator device.

As shown in FIG. 1 the baro-receptor stimulator device 10 includes as a power source a battery or set of batteries 11 which may be of any long-lasting type conventionally employed for powering medical electronic devices. Preferably such batteries as employed in implantable cardiac pacemaker or defibrillators are used. In the preferred embodiment of the baro-receptor stimulator device 10, the power source is either a cadmium or a lithium battery. The terminals of the battery 11 are connected to the input side of the voltage regulator 13. The regulator 13 smooths the battery output to produce a clean, steady output voltage, and provides enhancement thereof such as voltage multiplication or division if necessary for a specific application.

Regulator 13 supplies power to the logic and control component 15, which includes a micro-processor and controls the programmable functions of the device. Such programmability allows the output signal to be selectively crafted for application to the stimulating electrodes 22 (FIG. 2) to obtain the desired modulation of baro-receptor activity for treatment and control of the blood pressure.

Optionally a built-in antenna 17 enables communication between the baro-receptor stimulator device 10 and the external electronics (including both programming and monitoring devices) to permit the device to receive programming signals for parameter changes, and to transmit telemetry information to a programming wand or a display monitor. Once the system is programmed, it operates at the programmed settings until they are reprogrammed at the direction of an attending physician by means of the external computer and/or the programming wand.

Output component 18 comprises preferably an electromagnetic wave generator (not shown) or alternatively an ultrasound generator (also not shown) to produce electromagnetic waves or ultrasonic waves, respectively.

The baro-receptor stimulator device 10 may also be equipped with a power down circuit (not shown). The device remains in a reduced power state until the signal analysis unit 14 activates the logic and control unit 15 to override the power down circuit. Power down circuits employing semiconductor circuitry are well known in the integrated circuit field and such a circuit is readily available to be incorporated in the stimulator device of this invention by persons of ordinary skill in the art.

If episodes of the blood pressure fluctuations are relatively low for the patient this makes it possible to conserve considerable battery power between these episodes by shutting the device down into a steady state. It is anticipated that the power drain in the power down phase will be on the order of only a few nanoamperes. Hence, the average power consumed by the device can be reduced through power down so that the size of the battery may be quite small.

The reduced power requirement of the device in the interval between blood pressure fluctuations assures the availability of sufficient battery power to enable treatment over a much longer period than would otherwise be the case. The result is a significantly increased life of the device, a substantially increased interval between battery replacement and a considerable reduction in size of the device.

Figure 2:
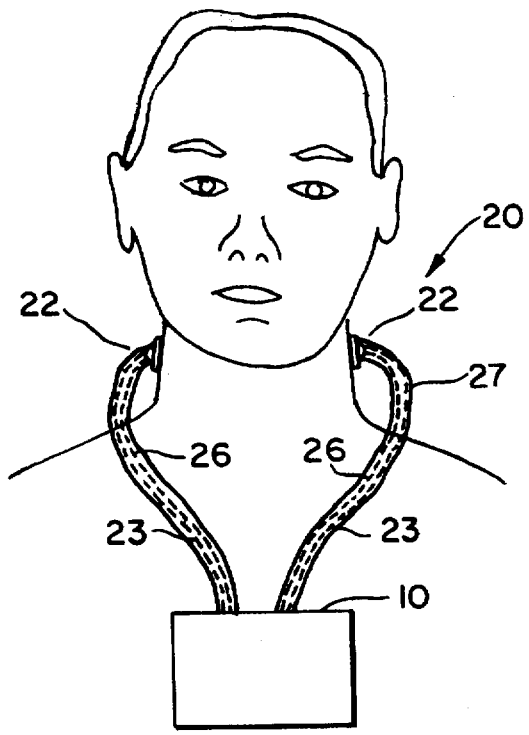
FIG. 2 is a fragmentary illustration of a preferred embodiment of the noninvasive blood pressure monitor and control apparatus according to the present invention.

The logic and control unit 15 of the baro-receptor stimulator device 10 controls an output circuit 18 which generates the programmed signal levels appropriate to the nature of the blood pressure elevation event. The output circuit 18 and its programmed output signal are coupled (directly capacitively, or inductively) to an electrical connector 19 on the housing 21 of the stimulator device 10 and to lead assembly 27 connected to sensing/stimulating electrodes or sensors 22 (FIG. 2). A sense signal analysis circuit 14 is provided within housing 21 with connections to the microprocessor in the logic and control component 15 and to the sensing/stimulating electrodes or sensors 22. The parameters of the stimulating signal of the implanted device may be calibrated by telemetry (i.e. the programming wand or a monitoring computer) according to the needs of the particular patient. The desired parameters are programmed into the microprocessor for delivery of the proper responsive signal needed to control the patient's blood pressure upon activation of the stimulator device 10.

Housing 21 in which the stimulator device is encased is made of plastic, and is preferably hermetically sealed, and is about 2" by 4" in size, which can be worn in a shirt pocket or clipped onto a belt.

FIG. 2 illustrates the preferred location of the sensing/stimulating electrodes or sensor 22, that is at the upper part of each side of the neck on the carotid artery. These sensors are about one millimeter (1 mm) or less in diameter size and are conductively connected to the distal end of insulated lead assembly 27 comprising monitor sensor lead 23 and stimulating lead 26. The sensors 22 are preferably adhesively attached and are flexible allowing the patient relatively free movement of the neck and chest. The inner diameter of the lead assembly 27 may be typically approximately two millimeters (2 mm) and about thirty to fifty centimeters (30–50 cm) long depending on the size of the patient.

The stimulator device 10 may be programmed with a personal computer (not shown) using suitable software based on the description herein and may include a programming wand (not shown). The wand and the software permit noninvasive communication with the stimulator device. The wand is preferably powered by internal batteries and provided with a "power-on" light to indicate sufficient power for communication. Another indicator light is preferably provided to show that data transmission is occurring between the wand and the stimulator device 10.

In treatment, the operation of the baro-receptor stimulator 10 uses different signal parameters to activate the baro-receptors situated at the upper part of each side of the neck to control high blood pressure. The patient's blood pressure is constantly monitored through sensors 22 adhesively attached to each side of the upper part of the neck as shown in FIG. 2, through monitor lead 23 to connect with input lead 12 of a preprogrammed baro-receptor stimulator device 10. If the blood pressure exceeds this preprogrammed limit, e.g. 120/80 millimeters of mercury (mmHg), the baro-receptor stimulator device 10 is automatically activated to emit electromagnetic or sound impulses directed to the carotid arteries through lead 26. Thus, the output signal of the baro-receptor stimulator device 10 is transferred to sensors 22 and stimulates the baro-receptors which lower the blood pressure. The higher the intensity of the signal the more pronounced is the blood pressure drop. Through a continuous feed-back mechanism, blood pressure is controlled through the preprogrammed baro-receptor stimulator device 10. For example, if the blood pressure falls at or below the preprogrammed 120/80 mmHg no impulses are emitted from the baro-receptor stimulator unit. Further, an upper limit can be programmed to, e.g., 160/90 mmHg and the logic and control system 15 of the baro-receptor stimulator device 10 will insure that such pressure is not exceeded and an alarm signal activated.

In another embodiment the baro-receptor stimulator device 10 may include a warning alarm in case of a faulty circuit or the inability of the baro-receptors to lower the blood pressure due to other medical factors. Such warning alarm, i.e. a continuous buzz and/or an intermittent beep, would alert the patient to seek immediate medical attention. The warning system could also be further connected to a control monitoring unit accessible to the patient's doctor connected via conventional telemetry.

Various features may be incorporated into the baro-receptor stimulator device 10 for the purpose of the safety and comfort of the patient. The programmable functions and capabilities of the baro-receptor stimulator device 10 is useful for both activation and monitoring functions. Beyond the essential functions of the device, the programming software may be readily structured to provide straight forward menu-driven operation to facilitate single and rapid programming while keeping the user fully informed of occurring at each step of a sequence. Programming capabilities should include capability to modify the adjustable parameters of the baro-receptor stimulator device 10 and its output signal, to test device diagnostic, and to store and retrieve telemetered data. It is desirable that when the baro-receptor stimulator device 10 is interrogated, the present state of the adjustable parameter is displayed on the monitor of the computer so that the programmer may then conveniently change any or all of those parameters at the same time; and, if a particular parameter is selected for change, all permissible values for that parameter are displayed so that the programmer may select an appropriate desired value for entry into the baro-receptor stimulator device.

Diagnostic testing should be implemented to verify proper operation of the device, and to indicate the existence of problems such as with communication, the battery or the lead/electrode impedance. A low battery reading, for example, would be indicative of imminent end of life of the battery.

The baro-receptors are stimulated at electromagnetic frequencies in the range of from about 0.5 to about 30 mHz.

The ultrasonic wave lengths useful according to this invention range is from about 0 to about 3 kHz.

Which specific embodiments have been disclosed herein, the invention is not limited thereto, and the language used in the specification is intended as descriptive rather than limiting, as those skilled in the art with the specifications therein without departing from the spirit of the invention claimed.

What is claimed is:

1. A noninvasive blood pressure monitor and control apparatus for use by a patient about the neck for stimulating the baro-receptors of said patient comprising a programmable baro-stimulator device adapted to receive input monitoring signals and to generate a programmed output signal upon activation of said device and a noninvasive conductive lead assembly connectable at its proximal end to said baro-stimulator device and having a sensor means at its distal end for noninvasive attachment to a surface of the skin on each side of the neck of said patient for stimulation of the baro-receptors of said patient to modulate the blood pressure, wherein the apparatus further includes:

sensor means coupled to said baro-stimulator device for detecting and stimulating blood pressure; and said baro-stimulator device comprising an electrical power source, signal analysis means connected to said sensor means for analyzing said blood pressure, programmable means associated with said signal analysis means for activating an output signal means for ultrasonic waves, and an output signal means for ultrasonic waves coupled with said sensor means for controlling the blood pressure by stimulating the baro-receptors according to specific programmed parameters.

2. The apparatus of claim 1 wherein said sensor means are attached to the skin surface at each side of the neck at the carotid artery.

3. The apparatus of claim 1 including a telemetry circuit for transmitting information to a monitor.

4. The apparatus of claim 1 including a warning device component comprising circuitry which provides a warning alarm indicating either a malfunction of a faulty circuit, a blood pressure increase, or both.

5. The apparatus of claim 1 wherein the blood pressure is constantly monitored when the apparatus is activated.

6. The apparatus of claim 1 wherein said input monitoring signal is transmitted to an external monitor.

7. The apparatus of claim 1 which is portable and which can be worn by said patient.

8. The apparatus of claim 1 including circuitry preventing an accidental reset of said specific parameters programmed.

9. A therapeutic method of noninvasively monitoring and controlling blood pressure in a patient which comprises the steps of:

monitoring said blood pressure;

detecting a rise in said blood pressure;

applying a programmed stimulus of ultrasonic waves to the baro-receptors in the arterial system of said patient in a manner to alleviate said raise in blood pressure in response to detection of such rise in said blood pressure.

* * * * *